(12) United States Patent
Chambers et al.

(10) Patent No.: US 11,076,646 B2
(45) Date of Patent: *Aug. 3, 2021

(54) ATHLETIC COLLAR

(71) Applicant: Guardian Athletics, LLC, Mankato, MN (US)

(72) Inventors: Jeffrey L. Chambers, North Mankato, MN (US); Derek N. Knees, Mankato, MN (US)

(73) Assignee: Guardian Athletics, LLC, Mankato, MN (US)

( * ) Notice: Subject to any disclaimer, the term of this patent is extended or adjusted under 35 U.S.C. 154(b) by 336 days.

This patent is subject to a terminal disclaimer.

(21) Appl. No.: 15/863,685

(22) Filed: Jan. 5, 2018

(65) Prior Publication Data
US 2018/0125126 A1    May 10, 2018

Related U.S. Application Data

(63) Continuation of application No. 14/539,649, filed on Nov. 12, 2014, now Pat. No. 9,888,732, which is a continuation of application No. 13/357,304, filed on Jan. 24, 2012, now Pat. No. 8,898,822.

(60) Provisional application No. 61/435,427, filed on Jan. 24, 2011.

(51) Int. Cl.
*A41D 13/05* (2006.01)
*A42B 3/04* (2006.01)
*A61F 5/055* (2006.01)

(52) U.S. Cl.
CPC ........ *A41D 13/0512* (2013.01); *A42B 3/0473* (2013.01); *A61F 5/055* (2013.01)

(58) Field of Classification Search
CPC .... A41D 13/0512; A42B 3/0473; A61F 5/055
See application file for complete search history.

(56) References Cited

U.S. PATENT DOCUMENTS

| | | |
|---|---|---|
| 3,477,425 A | 11/1969 | Grassl |
| 3,514,784 A | 6/1970 | McDavid |
| 3,855,631 A | 12/1974 | Ettinger |
| 4,067,063 A | 1/1978 | Ettinger |
| 4,287,613 A | 9/1981 | Schulz |
| 4,319,362 A | 3/1982 | Ettinger |
| 4,831,668 A | 5/1989 | Schulz |
| 4,872,216 A | 10/1989 | Wingo, Jr. |
| 4,926,503 A | 5/1990 | Wingo, Jr. |
| 4,985,931 A | 1/1991 | Wingo, Jr. |
| 5,029,341 A | 7/1991 | Wingo, Jr. |

(Continued)

FOREIGN PATENT DOCUMENTS

WO    WO-2009133579 A1    11/2009

OTHER PUBLICATIONS

"U.S. Appl. No. 13/357,304, Non Final Office Action dated Jan. 31, 2014", 19 pgs.

(Continued)

*Primary Examiner* — Richale L Quinn
(74) *Attorney, Agent, or Firm* — Schwegman Lundberg & Woessner, P.A.

(57) ABSTRACT

A device includes a collar and at least one pad. The collar is configured for wearing by a user, the collar having a plurality of pad receptacles. The at least one pad is configured for coupling with a selected one of the plurality of pad receptacles, the pad having an elastic portion configured to limit movement of a user.

20 Claims, 5 Drawing Sheets

(56) References Cited

U.S. PATENT DOCUMENTS

| | | | |
|---|---|---|---|
| 5,035,009 A | 7/1991 | Wingo, Jr. et al. |
| 5,129,101 A | 7/1992 | Douglas |
| 5,175,889 A | 1/1993 | Infusino |
| 5,263,203 A | 11/1993 | Kraemer et al. |
| 5,404,590 A | 4/1995 | Monica, Jr. |
| 5,483,698 A | 1/1996 | Douglas, Jr. |
| 5,520,619 A | 5/1996 | Martin |
| 5,588,957 A | 12/1996 | Martin, Sr. |
| 5,661,849 A | 9/1997 | Hicks |
| 5,728,054 A | 3/1998 | Martin |
| 5,797,863 A | 8/1998 | Kehnke |
| 5,993,403 A | 11/1999 | Martin |
| 6,036,664 A | 3/2000 | Martin et al. |
| 6,067,665 A | 5/2000 | DePalma et al. |
| 6,230,712 B1 | 5/2001 | Kohnke |
| 6,240,571 B1 | 6/2001 | Infusino |
| 6,245,033 B1 | 6/2001 | Martin |
| D465,067 S | 10/2002 | Ide et al. |
| D475,486 S | 6/2003 | Ide et al. |
| 6,726,643 B1 | 4/2004 | Martin |
| D498,344 S | 11/2004 | Mazzarolo |
| 6,817,029 B2 | 11/2004 | Mazzarolo |
| 6,934,971 B2 | 8/2005 | Ide |
| D511,026 S | 10/2005 | Ide et al. |
| D528,705 S | 9/2006 | Ide et al. |
| 7,117,537 B2 | 10/2006 | Mazzarolo |
| D542,919 S | 5/2007 | Leatt |
| 7,240,376 B2 | 7/2007 | Ide et al. |
| D552,742 S | 10/2007 | Leatt |
| 7,329,230 B2 | 2/2008 | Mazzarolo |
| 7,460,886 B2 | 12/2008 | Mazzarolo |
| 7,506,384 B2 | 3/2009 | Ide et al. |
| D592,310 S | 5/2009 | Leatt et al. |
| D603,099 S | 10/2009 | Bologna et al. |
| D603,100 S | 10/2009 | Bologna |
| D605,300 S | 12/2009 | Mazzarolo et al. |
| 7,823,220 B2 | 11/2010 | Mazzarolo |
| 7,846,117 B2 | 12/2010 | Leatt et al. |
| D631,167 S | 1/2011 | Leatt et al. |
| D633,623 S | 3/2011 | Leatt et al. |
| 7,900,284 B2 | 3/2011 | Mazzarolo |
| 7,921,472 B2 | 4/2011 | Mazzarolo |
| 7,930,773 B2 | 4/2011 | Ide et al. |
| 7,937,771 B2 | 5/2011 | Mazzarolo |
| 7,954,177 B2 | 6/2011 | Ide et al. |
| 7,993,293 B2 | 8/2011 | Leatt |
| 8,002,723 B2 | 8/2011 | Leatt |
| D649,649 S | 11/2011 | Leatt et al. |
| D651,353 S | 12/2011 | Mazzarolo |
| 8,162,865 B2 | 4/2012 | Mazzarolo |
| 8,162,866 B2 | 4/2012 | Mazzarolo |
| 8,214,929 B2 | 7/2012 | Kraemer et al. |
| 8,281,419 B2 | 10/2012 | Rietdyk et al. |
| 8,291,521 B2 | 10/2012 | Mazzarolo et al. |
| 8,347,415 B2 | 1/2013 | Mazzarolo |
| 8,370,968 B2 | 2/2013 | Kerr |
| D681,280 S | 4/2013 | Bologna et al. |
| D681,281 S | 4/2013 | Bologna et al. |
| 8,439,042 B2 | 5/2013 | Leatt et al. |
| 8,484,768 B2 | 7/2013 | Leatt et al. |
| 8,528,118 B2 | 9/2013 | Ide et al. |
| 8,549,674 B2 | 10/2013 | Kraemer et al. |
| 8,562,551 B2 | 10/2013 | Leatt |
| 8,615,819 B2 | 12/2013 | Kerr |
| 8,776,275 B2 | 7/2014 | Kordecki |
| 8,813,269 B2 | 8/2014 | Bologna et al. |
| 8,813,271 B2 | 8/2014 | Kraemer et al. |
| 8,832,871 B2 | 9/2014 | Mazzarolo et al. |
| 8,887,318 B2 | 11/2014 | Mazzarolo et al. |
| 8,898,822 B2 | 12/2014 | Chambers et al. |
| 8,938,817 B1 | 1/2015 | Baldi |
| 8,938,818 B2 | 1/2015 | Ide et al. |
| 8,938,820 B2 | 1/2015 | Mazzarolo et al. |
| 9,132,334 B2 | 9/2015 | Ide et al. |
| 9,185,945 B2 | 11/2015 | Rietdyk |
| 9,220,311 B1 | 12/2015 | Baldi |
| D752,821 S | 3/2016 | Bologna |
| D752,822 S | 3/2016 | Bologna |
| 9,289,024 B2 | 3/2016 | Withnall et al. |
| 9,314,063 B2 | 4/2016 | Bologna et al. |
| 9,332,794 B2 | 5/2016 | Mazzarolo et al. |
| 9,352,210 B2 | 5/2016 | Kordecki |
| D764,716 S | 8/2016 | Bologna |
| 9,457,257 B2 | 10/2016 | Ide et al. |
| D787,748 S | 5/2017 | Bologna |
| 9,656,148 B2 | 5/2017 | Bologna et al. |
| 9,756,889 B2 | 9/2017 | Infusino et al. |
| 9,763,488 B2 | 9/2017 | Bologna et al. |
| 9,770,060 B2 | 9/2017 | Infusino |
| 9,801,424 B2 | 10/2017 | Mazzarolo et al. |
| D803,483 S | 11/2017 | Bologna |
| D804,105 S | 11/2017 | Bologna |
| 9,888,732 B2 | 2/2018 | Chambers et al. |
| 2007/0156072 A1 | 7/2007 | Leatt |
| 2007/0163032 A1 | 7/2007 | Kerr |
| 2010/0056968 A1 | 3/2010 | Mazzarolo |
| 2010/0088808 A1 | 4/2010 | Rietdyk et al. |
| 2010/0121238 A1 | 5/2010 | Mazzarolo |
| 2010/0235973 A1 | 9/2010 | Mazzarolo |
| 2010/0251467 A1 | 10/2010 | Leatt |
| 2010/0251468 A1 | 10/2010 | Mazzarolo |
| 2010/0263111 A1 | 10/2010 | Leatt et al. |
| 2010/0263112 A1 | 10/2010 | Mazzarolo et al. |
| 2011/0004980 A1 | 1/2011 | Leatt et al. |
| 2011/0041240 A1 | 2/2011 | Mazzarolo |
| 2011/0277221 A1 | 11/2011 | Ide et al. |
| 2012/0291189 A1 | 11/2012 | Chambers |
| 2013/0000023 A1 | 1/2013 | Kraemer et al. |
| 2013/0061375 A1 | 3/2013 | Bologna et al. |
| 2013/0152288 A1 | 12/2013 | Kerr |
| 2014/0007327 A1 | 1/2014 | Ide et al. |
| 2014/0020162 A1 | 1/2014 | Kraemer et al. |
| 2014/0109305 A1 | 4/2014 | Kerr |
| 2014/0150169 A1 | 6/2014 | Ide et al. |
| 2014/0221161 A1 | 8/2014 | DePalma |
| 2014/0223643 A1 | 8/2014 | Infusino et al. |
| 2014/0223644 A1 | 8/2014 | Bologna et al. |
| 2015/0067953 A1 | 3/2015 | Chambers et al. |
| 2015/0128334 A1 | 5/2015 | Mazzarolo et al. |
| 2015/0173433 A1 | 6/2015 | Mazzarolo et al. |
| 2016/0174641 A1 | 6/2016 | Leatt et al. |
| 2017/0056753 A1 | 3/2017 | Kerr |
| 2017/0172242 A1 | 6/2017 | Leatt et al. |
| 2017/0202279 A1 | 7/2017 | Mazzarolo et al. |
| 2017/0314963 A1 | 11/2017 | Ballantyne et al. |

OTHER PUBLICATIONS

"U.S. Appl. No. 13/357,304, Notice of Allowance dated Jul. 29, 2014", 8 pgs.

"U.S. Appl. No. 13/357,304, Response filed Jun. 2, 2014 to Non Final Office Action dated Mar. 31, 2014", 9 pgs.

"U.S. Appl. No. 14/539,649, Non Final Office Action dated Feb. 10, 2017", 17 pgs.

"U.S. Appl. No. 14/539,649, Notice of Allowance dated Oct. 3, 2017", 13 pgs.

"U.S. Appl. No. 14/539,649, Preliminary Amendment filed Nov. 14, 2014", 7 pgs.

"U.S. Appl. No. 14/539,649, Response filed Jun. 12, 2017 to Non Final Office Action dated Feb. 10, 2017", 14 pgs.

U.S. Appl. No. 13/357,304, filed Jan. 24, 2012, Athletic Collar, U.S. Pat. No. 8,898,822.

U.S. Appl. No. 14/539,649, filed Jan. 24, 2012, Athletic Collar.

U.S. Pat. No. 8,898,822, filed Jan. 24, 2012, Athletic Collar.

ATHLETIC COLLAR

CLAIM OF PRIORITY

This patent application is a continuation of U.S. Ser. No. 14/539,649, filed on Nov. 12, 2014 and entitled "ATHLETIC COLLAR," which is a continuation of U.S. Ser. No. 13/357,304, filed on Jan. 24, 2012 and entitled "ATHLETIC COLLAR," which claims the benefit of priority, under 35 U.S.C. Section 119(e), to U.S. Provisional Patent Application Ser. No. 61/435,427, entitled "ATHLETIC COLLAR AND GARMENT," filed on Jan. 24, 2011, all of which are hereby incorporated by reference herein in their entirety.

BACKGROUND

A brachial plexus injury, or BPI, is a common injury in contact sports. It is reported to affect as many as 65% of collegiate football players at some point in their career. The brachial plexus are nerves that leave the cervical vertebrae and extend through the neck and upper shoulder to peripheral structures. The brachial plexus is a complex arrangement of nerves that are found underneath the clavicle or collarbone and transmit motor and sensory impulses to the brain. Acute trauma to this group of nerves can elicit a painful burning or stinging sensation throughout the entire upper extremity, hence giving it the name "burner or stinger."

OVERVIEW

An example of the present subject matter includes a protective neck collar configured for use by an athlete, such as a football player, a motorcyclist, a rodeo event performer, or other contact sport athlete.

An example of the present subject matter can be effective in treating a BPI, sometimes known as a "burner" or a "stinger." The pathology of a BPI includes a stretch or impingement to the nerves which make up the brachial plexus and/or a traction or compression of a nerve root exiting the cervical spine through the foramen between cervical vertebrae.

Some athletic neck collars severely limit head mobility. One example of a collar restricts head movement and may impair the ability of the user to see in a forward direction.

Current technology for a football athlete includes a neck collar having a structure that limits mobility of the head and neck. The collar is worn in a position that restricts movement beyond an excessive range of motion causing the BPI. Movement is restricted such that the eyes cannot be raised and forward vision is severely limited. This configuration leads to a vulnerable head and neck position that can lead to more serious injury.

An example of the present subject matter can protect an athlete whose head and neck have been forced into a position from a blow causing a BPI. The present subject matter is configured to prevent excessive motion in multiple directions. One example is adjustable and can be configured to prevent excessive motion of the head and neck and decelerate the harmful force which causes the painful BPI. Since the head and neck remain mobile, the athlete is able to maintain visibility necessary to play football. An example of the present subject matter reduces the risk of permanent damage or disability from repeated blows during contact. An example of the present subject matter provides protection in various directions without complete restriction of the head and neck.

One example is configured to reduce the occurrence and recurrence of brachial plexus injuries by limiting the excessive motions which cause the injury. One example is configured to limit movement and decelerate motion which causes the injury, including extension and oblique motions, without restricting mobility of the head and neck. An example can be tailored for use in sports such as hockey and competitive bull riding.

An example of the present subject matter is configured to protect athletes, in contact sports, from temporary and permanent injury to the cervical spine and upper extremity nerves. It is designed to limit mechanisms which cause excessive motion of the head and neck in multiple directions. One example includes a structure formed using a two-shot plastic mold. A plurality of bumpers can be positioned on the structure to limit, but not restrict, motion of the head and neck. A bumper can include an inflatable air bladder having dimensions of approximately 1¼ inch by 3 inch section of soft material that can be individually inflated with air. A bumper is configured to decelerate the movement of the head and neck.

An example of the present subject matter is configured to attach directly to the body, thus allowing it to function independent of shoulder pad movement. In one example, a garment is used to secure the device to the athlete. The garment can include a compression-type shirt.

The bumper can include an inflatable air bladder that is individually affixed to the base of the collar. The bumper can be configured for positioning in a cavity of the device. An inflatable bumper can include a receptacle to receive air, allowing inflation. In various examples, one, two, or three bumpers can be provided and inflated to a selected pressure to limit or prevent motion of the neck in a particular direction. An example of the present subject matter decelerates and limits motion in the specific direction which causes the injury without restricting head and neck movement. The air bladders can be inflated to a predetermined pressure, depending on the size of the neck or the direction for which movement is to be limited.

An example of the present subject matter is configured to limit and decelerate the motion of the head and neck following a blow and to allow unrestricted neck motion to the point that the head and neck are not locked in an immovable position. One example provides shock absorption, better control of head motion, and without the fulcrum effect typically caused by a strike. One example is configured to prevent BPIs caused by head and neck movement in a direction which can limit the use of upper extremity following repeated injury.

These examples can be combined in any permutation or combination. This overview is intended to provide an overview of subject matter of the present patent application. It is not intended to provide an exclusive or exhaustive explanation of the invention. The detailed description is included to provide further information about the present patent application.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Some signs or symptoms associated with BPI include pain in the neck and shoulder region, an intense "burning" sensation, paresthesia, or numbness radiating from the shoulder and neck to the fingers, weakness or heaviness in the extremity, diminished pulse or blood flow throughout the upper extremity, and diminished reflexes in upper extremity.

The BPIs sustained in contact sports are usually the result of biomechanical factors that lead to nerve traction or compression. The onset of the injury is typically caused either by a stretching of the brachial plexus itself (brachial plexus traction), contusion of the brachial plexus itself (brachial plexus compression), cervical nerve root traction, or cervical nerve root compression (impingement). Stretching of the brachial plexus or cervical nerve root occurs when the head is forced laterally while the opposite shoulder is depressed, such as when tackling in football.

Figure 1A:
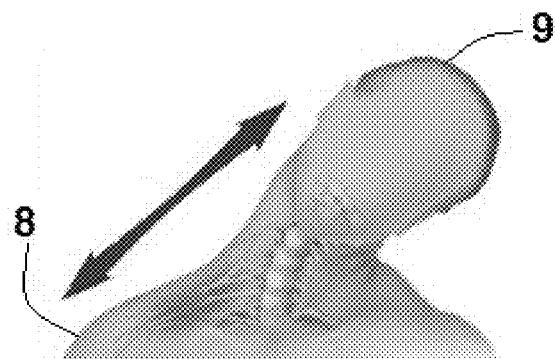
FIGS. 1A, 1B, and IC illustrate mechanics of an injury.

FIG. 1A illustrates movement that can result in a BPI. This force results in traction on the nerves on the opposite side of where the lateral bending is occurring. FIG. 1A illustrates traction to the brachial plexus from ipsilateral shoulder depression and contralateral lateral neck flexion. In FIG. 1A, opposite shoulder 8 is moved downward and head 9 moves in a sideways direction.

Figure 1B:
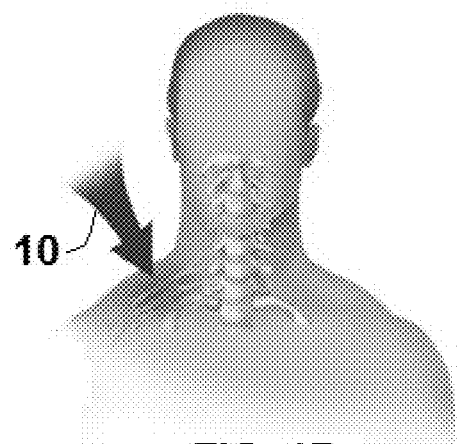

Arrow 10 in FIG. 1B illustrates a direct blow to the supraclavicular fossa at Erb's point.

Figure 1C:
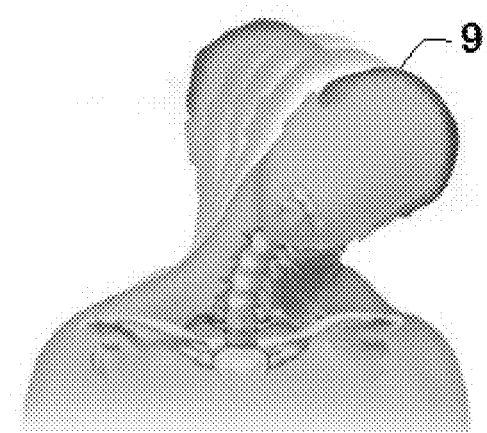

FIG. 1C illustrates compression of the cervical roots or brachial plexus from ipsilateral lateral flexion and hyperextension. A cervical root compression or brachial plexus compression occurs on the side of the body toward where the neck is bent. When head 9 is pushed to the side, the nerve roots are compressed between the vertebrae or the brachial plexus between the clavicle and muscles directly underneath.

Repeated low-intensity traction of the brachial plexus results in low blood-flow to the plexus and may cause permanent damage to the nerves. In most cases, the symptoms are usually temporary and last only a few minutes, but can become recurrent and lead to permanent damage. Most experts agree that acute, isolated BPIs are common and pose no significant harm, however chronic and recurrent BPIs can lead to an event causing permanent deficits in the future. These experts agree that if play modification fails to resolve the symptoms, withdrawal from the sport may be necessary to prevent long-term damage.

A BPI tends to lead to chronic episodes of painful injury. One study of college football players found that 87 percent of those who had sustained a "burner or stinger" had a recurrence. Another study found that of 36 athletes with neck injuries causing time loss from sports participation (most symptoms were consistent with burners), 15 (42 percent) of those athletes experienced subsequent neck injuries. According to some, over 70% of the athletes who had reported that they had sustained a BPI did not report the injury to anyone. The risk of permanent nerve injury from recurrent burners has not yet been determined. In light of the high incidence of burners, this risk appears to be low. However, burners can clearly lead to a chronic syndrome that limits athletic participation.

Not only are BPIs debilitating for the athletes in a physical sense, many times it becomes a costly endeavor for the family as well. Stingers with prolonged neurological symptoms are a common reason for high school and collegiate football players to be referred to emergency rooms and orthopaedic clinics for evaluation of the cervical spine.

Figure 2:
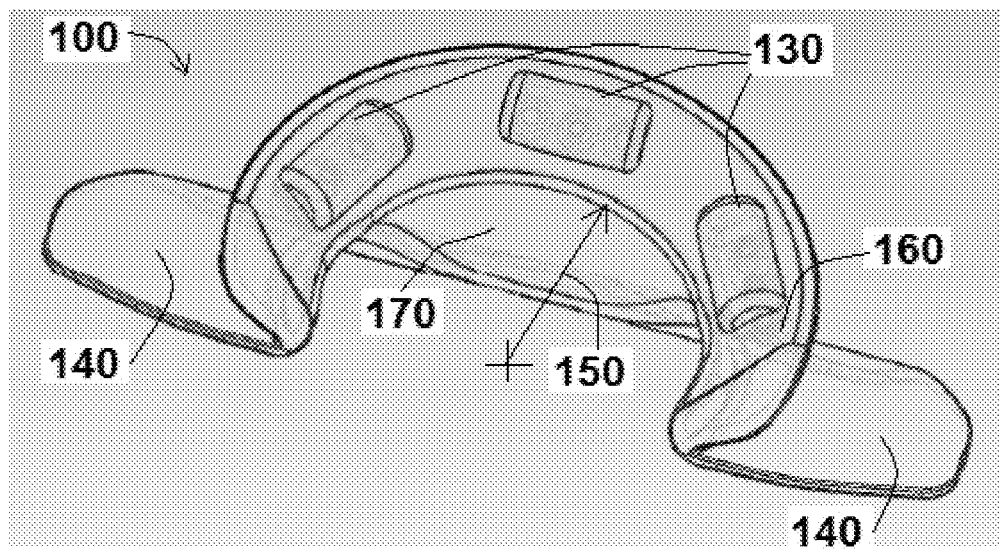
FIG. 2 illustrates a view of a device according to one example.

FIG. 2 illustrates collar 100 according to one example. Collar, or device, 100 in this example includes an upper flange 160 spaced apart from shoulder flaps 140 by riser 170.

Upper flange 160 is configured to encircle a portion of a neck of a user. In the example shown, upper flange 160 encircles the sides and rear of the neck and is fitted with three bumpers 130.

Bumper 130 includes an inflated shock-absorbing unit that resists a compression load and distributes an impact force over the upper flange 160. In the example shown, each bumper 130 includes a generally cylindrical, air pressurized element fitted into a corresponding receptacle of upper flange 160.

Upper flange 160 is held in a position near the neck of the user by riser 170. Riser 170 partially encircles the neck and is contoured to retain the upper flange 160 in a relatively high position to the rear of the user and gradually taper to a lower position near the front of the user. In one example, riser 170 is formed integral with upper flange 160. Riser 170, like upper flange 160, is fabricated of a substantially rigid material and is configured to withstand impact forces associated with athletic activity.

In the example shown, riser 170 is coupled to a left-side shoulder flap 140 and a right-side shoulder flap 140. Shoulder flap 140 is configured to distribute compressive loads from riser 170 to the musculoskeletal frame of the user. Shoulder flap 140 provides a broad contact area and also provides an anchor mechanism by which collar 100 can be affixed to the user. Shoulder flap 140 can include a molded plastic flange that is integral with riser 170.

Upper flange 160 includes an inside effective diameter 150 that provides sufficient clearance to allow substantially normal movement of the neck. In particular, collar 100 allows the neck to bend in a forward direction without restriction. Head movement to either side or to the rear is limited by contact between the helmet (or the head) and bumpers 130 affixed to upper flange 160 or upper flange 160 itself.

Figure 3:
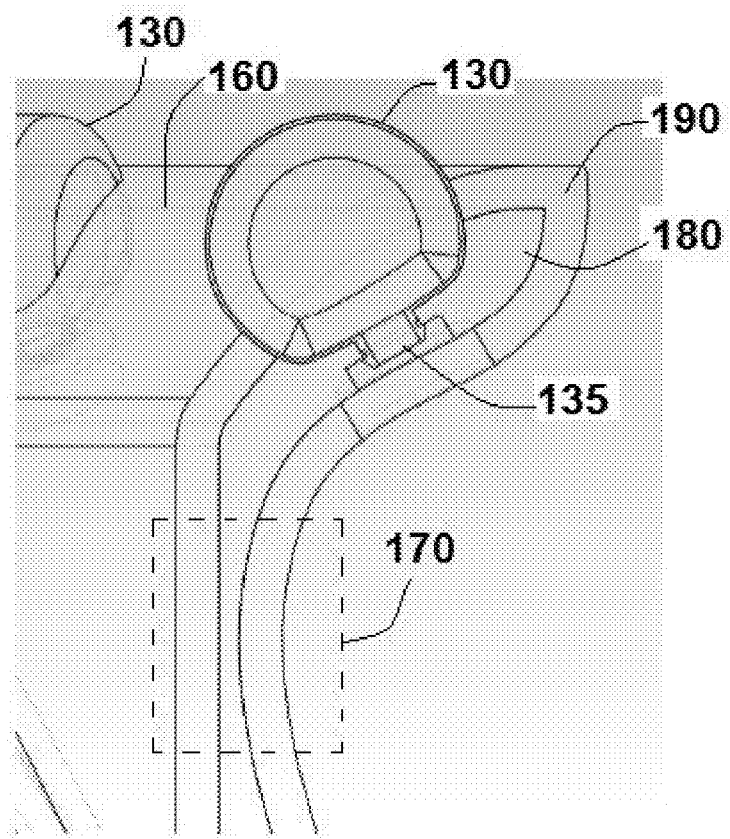
FIG. 3 illustrates a section view of a device according to one example.

FIG. 3 illustrates a partial sectional view of collar 100. The figure illustrates two bumpers 130 coupled to upper flange 160. Upper flange 160 is integral with riser 170 and includes inner structure 180 and outer structure, or overmold 190. The durometer of inner structure 180 and outer structure 190 can be the same or different. In one example, inner structure 180 includes a hard plastic and outer structure 190 includes a soft plastic or soft rubber.

Bumper 130 is fitted within a receptacle or cavity of an upper surface of upper flange 160 and is retained in position by post 135 and a corresponding aperture in upper flange 160.

Collar 100, in the examples shown, includes a molded plastic structure. A multi-shot molding operation can be used to fabricate collar 100. For example, collar 100 can include an inner structure fabricated of a rigid plastic and an overmolded soft rubber outer structure.

Figure 4:
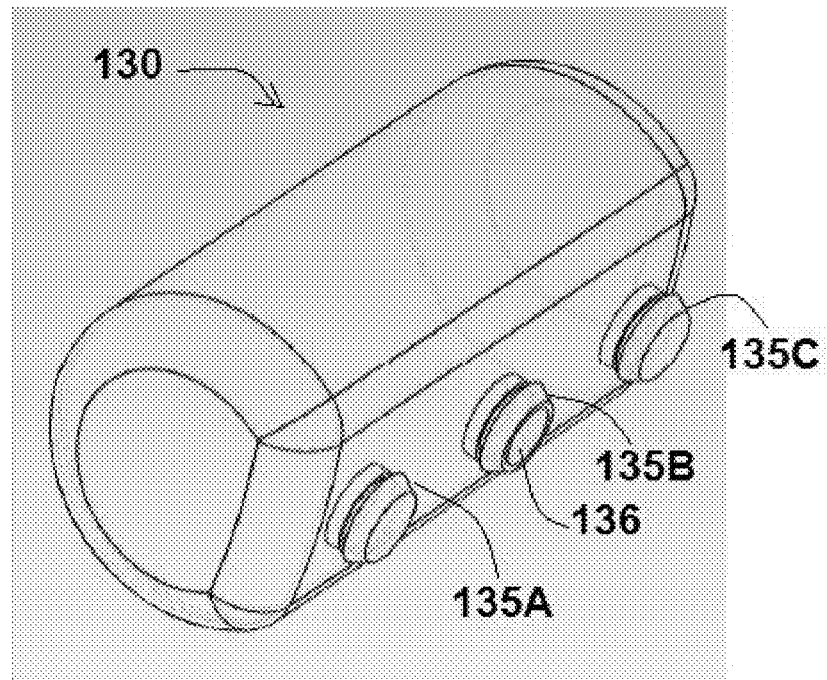
FIG. 4 illustrates a bumper according to one example.

FIG. 4 illustrates a view of bumper 130 according to one example. In the example shown, bumper 130 includes an elastic pad having posts 135A, 135B, and 135C. Posts 135A, 135B, and 135C provide protuberances that engage corresponding apertures in upper flange 160. Posts 135A, 135B, and 135C include a barbed feature to facilitate retention.

Bumper 130 can include a thin walled bladder having pressurized air, foam, gel, or other shock-absorbing material.

In the example shown, bumper 130 includes a filler port or septum 136. Septum 136 includes a self-closing material that allows insertion and retraction of an inflation needle and allows a user to selectively pressurize the bladder with air. The user can select the resilience of bumper 130 based on air inflation pressure selected.

In the example shown, bumper 130 includes a generally cylindrical bladder having a flatted surface. The flatted surface, in the region around posts 135A, 135B, and 135C, is configured to stabilize the bumper within a receptacle of the collar.

Figure 5A:
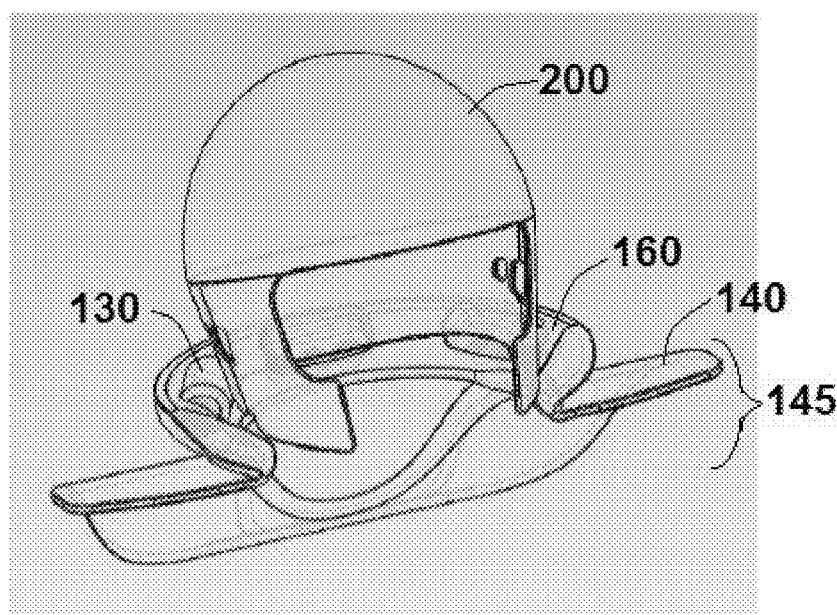
FIGS. 5A, 5B, and 5C illustrate views of a device according to one example.
Figure 5B:
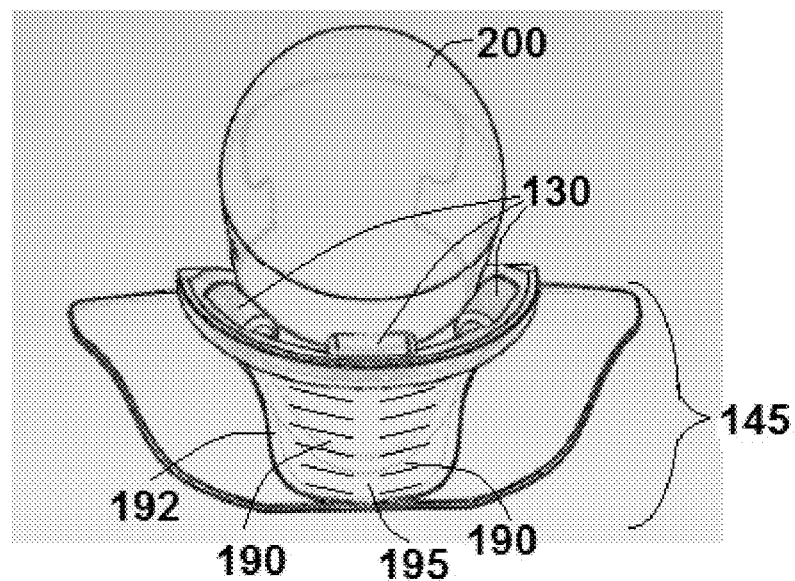
Figure 5C:
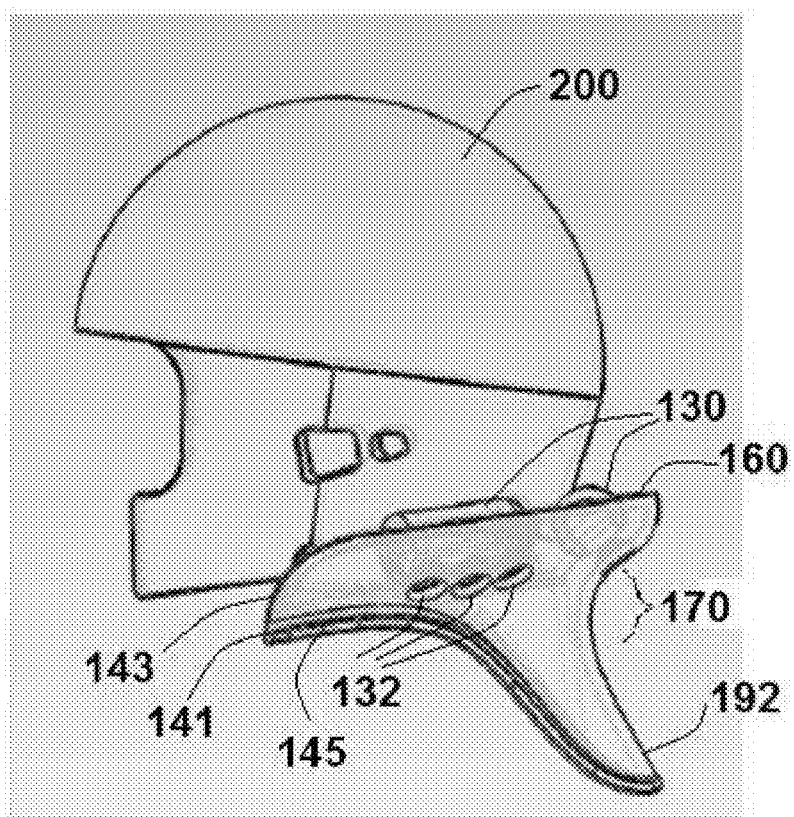

FIGS. 5A, 5B, and 5C illustrate views of a collar in conjunction with protective helmet 200. FIG. 5A illustrates a view generally from the front, FIG. 5B illustrates a view from the rear, and FIG. 5C illustrates a side view.

In FIG. 5A, bumper 130 is shown in upper flange 160. Freedom of movement of helmet 200 is limited by the clearance between the lower region of helmet 200 and bumper 130 or between the lower region of helmet 200 and upper flange 160. Lower flange 145 is coupled to upper flange 160 by riser 170 (not shown in this figure). Lower flange 145 is configured for placement atop the shoulders of the user and, in the example shown, includes shoulder flap 140.

FIG. 5B illustrates a view of helmet 200 and bumpers 130. Lower flange 145, as shown in the figure, includes a view of back pad 192. Back pad 192, includes raised portion 195 flanked by contact surfaces 190. Contact surfaces 190 are configured to contact the back surface of the user and raised portion 195 is configured to provide clearance for the spinal column of the user. When fitted to a user, a portion of a downward directed impact force applied to bumpers 130 is conveyed to the upper flange, to back pad 192, and to the back of the user via contact surfaces 190. A substantial portion of an impact force is directed away from the spinal column.

FIG. 5C illustrates a side view of helmet 200 and bumpers 130. In the figure, bumpers 130 are positioned in upper flange 160 at a location near the lower regions of helmet 200.

Upper flange 160 is canted forward by riser 170. A rear portion of upper flange 160 is elevated relative to a forward portion of the upper flange 160. Forward edge 143 of the collar gradually tapers downward to provide a smooth transition to allow limited range of head motion in the sideways direction to a full range of motion in the forward direction.

As shown in the figure, bumper 130 is retained by apertures 132 in a portion of the upper flange 160. In addition, the figure illustrates back pad 192 descending from riser 170. Lower flange 145 includes back pad 192 and shoulder flaps 140. Edge 141 denotes a forward edge of shoulder flap 140.

Figure 6:
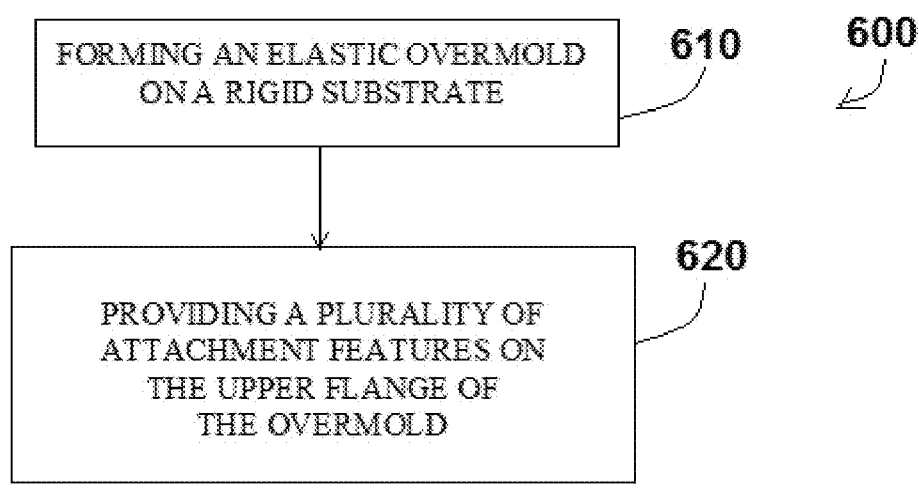
FIG. 6 illustrates a flow chart of a method according to one example.

FIG. 6 illustrates method 600 for manufacturing a collar, according to one example. At 610, method 600 includes forming an elastic overmold on a rigid substrate. In one example, forming the overmold can include implementing an injection molding process using a hard plastic inner structure. At 620, method 600 includes providing a plurality of attachment features on the upper flange of the overmold. In one example, this includes providing apertures configured to receive a corresponding feature of a bumper. The apertures can include blind holes or through holes. In one example, the attachment features include a portion of a hook-and-loop fastener system and the corresponding feature of the bumper can include the other portion of the hook-and-loop system.

ADDITIONAL NOTES AND EXAMPLES

An example of the present subject matter is directed to reduce or mitigate injury caused by a brachial plexus stretch, impingement or cervical nerve root traction or compression.

One example includes a mechanism configured to decelerate head and neck motion in a user-specified direction. An example is configured to block motion at the extreme of the direction. An example includes a collar configured to attach to a player's body and not directly coupled to the shoulder pads, therefore, maintaining a more stable position during a blow or hit. In one example, the shoulder pads are free to move and the collar will not move.

The shoulder flange can be held in position on the user by a tight fitting garment, strap, or harness. For example, a football player may wear the collar under the protective shoulder pads or under a tight fitting shirt.

One example of the present subject matter is configured to attach to the user in a manner independent of shoulder pads or allow movement independent of the shoulder pads.

One example of the present subject matter is configured to decelerate and limit the extreme motion in the direction the head and neck moves which causes the injury to the brachial plexus or cervical nerve root without limiting mobility of the head and neck.

In one example, the inner structure can include a nylon or nylon-based material and the outer structure can include a rubber overmold.

The present subject matter can be configured to provide various levels of protection. For example, the number and placement of the bumpers and internal air pressure of the bumpers can be selected based on the nature of the play and the user choice. For example, a user may choose to wear a collar having side bumpers installed with one bumper having a first pressure and a second bumper having a second and different air pressure.

Various embodiments can include a collar having three elastic bumpers or pads. The bumpers can be selectively removed and installed by a user. For example, a user can opt to install a single bumper in a particular location, two bumpers in selected locations, or three bumpers in the locations shown. A greater or lesser number of bumpers can be provided.

In one example, the collar includes an overmolded portion of rubber or plastic. The overmolded portion is configured to provide a cushioned surface. Other methods of fabrication are also contemplated, including rotary molding.

The upper flange is configured to provide a contoured surface for contacting the helmet in order to protect the user. The lower flange, including shoulder flaps and back pad, can be configured to provide support as needed. In addition, the lower flange can be tailored to provide clearance and not impair player mobility. For example, the shoulder flaps can be trimmed or extended to provide good support and flexibility.

The bumpers can be configured as generally cylindrical bladders as shown. In other examples, the bumpers are cylindrical or spherical shaped elements and can be attached by a hook-and-loop fastener (such as Velcro), adhesive, snaps, or other fastener (temporary or permanent). The bumpers are located on the upper flange and provide deceleration.

In one example, the lower region of the lower flange includes a surface configured to exert a substantial portion of a compressive force carried by the riser to regions adjacent a spine of the user.

In one example, the collar has an open front region sized to pass around a neck with sufficient clearance to allow head movement within a predetermined range and to prevent head movement beyond the predetermined range. The collar can be fabricated of a unitary, seamless material and can be fabricated without a split, a hinge, or a joint.

Bumpers can be selected and positioned to provide clearance between the helmet and the upper flange. The placement, number, and inflation level of the bumpers can be adjusted to accommodate different head, helmet, and player sizes.

Example 1 can include a collar having an upper flange, a shoulder flange, and a riser. The upper flange is configured to encircle a portion of a neck of a user. The upper flange is configured to limit movement of a helmet worn by the user in directions corresponding to the portion. The upper flange is configured to allow unrestricted movement of the helmet in a forward direction and has forward side segments disposed on opposite sides and configured to provide gradually increasing restriction of sideways movement of the helmet. The upper flange includes a rear segment configured to restrict rearward movement of the helmet. The shoulder flange is configured to be secured to a shoulder of the user. The shoulder flange has a substantially rigid surface configured to distribute a load to the shoulder and to an upper back region of the user. The riser is coupled to the upper flange and coupled to the shoulder flange. The riser has a rigid structure configured to convey a compressive force applied to the upper flange to the shoulder flange and is configured to hold the upper flange in a position to allow extension of the neck to a position above a spine of the user and to prevent hyperextension of the neck.

Example 2 can include, or can optionally be combined with the subject matter of Example 1, to optionally include least one bumper coupled to the upper flange.

Example 3 can include, or can optionally be combined with the subject matter of Example 2 to optionally include at least one bumper including an inflatable bladder.

Example 4 can include, or can optionally be combined with the subject matter of one or any combination of Examples 2 or 3 to optionally include wherein the at least one bumper is coupled to the upper flange by a fastener.

Example 5 can include, or can optionally be combined with the subject matter of Example 4 to optionally include wherein the fastener includes a hook and loop fastener.

Example 6 can include, or can optionally be combined with the subject matter of Example 5 wherein the fastener includes a post and a receptacle.

Example 7 can include, or can optionally be combined with the subject matter of one or any combination of Examples 2-6 wherein the at least one bumper includes a foam filled bladder.

Example 8 can include, or can optionally be combined with the subject matter of one or any combination of Examples 1-7 wherein the upper flange, lower flange, and riser are injection molded.

Example 9 can include, or can optionally be combined with the subject matter of one or any combination of Examples 1-8 wherein the upper flange, lower flange, and riser include a rigid core and an elastic overmold.

Example 10 can include, or can optionally be combined with the subject matter of one or any combination of Examples 1-9 wherein the shoulder flange includes a void configured to reduce loading on a spinal column of the user.

Example 11 can include, or can optionally be combined with the subject matter of one or any combination of Examples 1-10 wherein the shoulder flange includes a forward edge configured for positioning atop the shoulders of the user.

Example 12 can include a method of manufacturing comprising forming and providing. The method can include forming an elastic overmold on a rigid substrate. The rigid substrate can have a riser and the overmold can have an upper flange and a shoulder flange. The upper flange can be configured to limit movement of a helmet worn by a user in directions corresponding to the portion. The upper flange can be configured to allow unrestricted movement of the helmet in a forward direction and having forward side segments disposed on opposite sides and configured to provide gradually increasing restriction of sideways movement of the helmet, and having a rear segment configured to restrict rearward movement of the helmet. The shoulder flange can be configured to be secured to a shoulder of the user. The shoulder flange can have a substantially rigid surface configured to distribute a load to the shoulder and to an upper back region of the user. The riser can be coupled to the upper flange and coupled to the shoulder flange. The riser can have a rigid structure configured to convey a compressive force applied to the upper flange to the shoulder flange and configured to hold the upper flange in a position to allow extension of the neck to a position above a spine of the user and to prevent hyperextension of the neck. The method can include providing a plurality of attachment features on the upper flange. The attachment features can be configured to receive at least one elastic bumper. The elastic bumper can be configured to further limit movement of the helmet.

Example 13 can include, or can optionally be combined with the subject matter of Example 12, wherein forming includes injection molding.

Example 14 can include, or can optionally be combined with the subject matter of one or any combination of Examples 12 or 13 to optionally include wherein providing the plurality of attachment features includes providing receptacles, each receptacle having an aperture configured to receive a corresponding post of a bumper.

Example 15 can include, or can optionally be combined with the subject matter of one or any combination of Examples 12 to 14 to optionally include wherein forming the elastic overmold includes forming a soft rubber layer.

Example 16 can include an apparatus including an upper flange, a riser, and a shoulder flange. The upper flange can be configured to partially encircle and limit movement of the neck of a user. The upper flange can have a forward open region and angular side regions that gradually transition to a high back region. The riser can be coupled to the upper flange. The riser can be configured to hold the upper flange in alignment with the neck. The shoulder flange can be configured to distribute a compressive force exerted on the upper flange to a shoulder of the user. The shoulder flange can be configured to attach to a garment of the user. The upper flange can be configured to preclude hyperextensive movement of the neck.

Example 17 can include, or can optionally be combined with the subject matter of Example 16, to optionally include a plurality of elastic bumpers affixed to the upper flange.

Example 18 can include, or can optionally be combined with the subject matter of one or any combination of Examples 16 or 17, to optionally include wherein at least one elastic bumper has a repositionable location.

Example 19 can include, or can optionally be combined with the subject matter of one or any combination of Examples 16 to 18, to optionally include wherein the elastic bumper includes an inflatable bladder.

Example 20 can include, or can optionally be combined with the subject matter of one or any combination of Examples 16 to 19, to optionally include wherein the upper flange, the riser, and the shoulder flange are injection molded.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A collar comprising:
a lower flange configured to partially encircle a neck of a user, the lower flange including:
a back pad configured to contact an upper back region of the user, and
a shoulder flap configured to provide a contact surface to be placed atop a shoulder of the user;
an upper flange coupled to the lower flange and configured to encircle a portion of the neck and to allow unrestricted forward movement of a head of the user, wherein the upper flange includes:
a first side segment opposing a second side segment, the first side segment and the second side segment configured to limit movement of the head in a sideways direction, and a rear segment configured to limit movement of the head in a rearward direction; and
a plurality of bumpers affixed to the upper flange each of the plurality of bumpers spaced from others of the plurality of bumpers, wherein at least a first one of the plurality of bumpers is located on the upper flange and is configured to exert a force on a back of the head during extension of the neck in a rearward direction to dampen movement of the head and at least a second one of the plurality of bumpers is located on the upper flange and is configured to exert a force on a side of the head during lateral movement of the neck in a sideways direction to dampen movement of the head, wherein the plurality of bumpers do not extend forward of the upper flange to allow for unrestricted forward movement of the head of the user.

2. The collar of claim 1, wherein the first side segment and the second side segment provide a gradually increasing restriction of sideways movement of the head, and the rear segment provides a gradually increasing restriction of rearward movement of the head.

3. The collar of claim 1, wherein the position of the second one of the plurality of bumpers is to the side of the head of the user.

4. The collar of claim 3, wherein the second one of the plurality of bumpers is positioned between a location lateral to an ear and a location lateral to a top of the neck of the user, and the first one of the plurality of bumpers is positioned between a location posterior to an ear and a location posterior to a top of the neck.

5. The collar of claim 1, wherein the location of the plurality of bumpers on the upper flange allows for contact with a back of a helmet or a side of the helmet worn by the user during lateral movement of the neck in a sideways direction or extension of the neck in a rearward direction.

6. The collar of claim 5, wherein the location of the plurality of bumpers on the upper flange avoids contacting a bottom edge of the helmet worn by the user, the plurality of bumpers provide shock absorption without a fulcrum effect on the head.

7. The collar of claim 1, wherein the location of the plurality of bumpers on the upper flange allows for contact with a lower region of the head, or allows for contact with a helmet worn by the user, during lateral movement of the neck in a sideways direction or during extension of the neck in a rearward direction.

8. The collar of claim 1, wherein the position of the first side segment and the second side segment are configured to provide clearance between the head, or a helmet worn by the user, and the first and second side segments and to limit sideways movement of the head, and the rear segment is positioned to provide clearance between the rear segment and the head or helmet and to limit rearward movement of the head.

9. The collar of claim 1, wherein the location of the plurality of bumpers on the upper flange mitigates hyperextension and lateral hyperflexion of the neck.

10. The collar of claim 1, wherein the plurality of bumpers are coupled to the upper flange by a fastener.

11. The collar of claim 10, wherein the fastener includes a hook and loop fastener.

12. The collar of claim 10, wherein the fastener includes a post and a receptacle.

13. The collar of claim 1, wherein the back pad is configured to reduce loading on a spinal column of the user.

14. The collar of claim 1, wherein the plurality of bumpers are selectively positionable at various locations on the upper flange.

15. A collar comprising:
a lower flange configured to partially encircle a neck of a user, the lower flange including:
a back pad configured to contact an upper back region of the user, and
a shoulder flap configured to provide a contact surface to be placed atop a shoulder of the user;
an upper flange coupled to the lower flange and configured to encircle a portion of the neck and to allow unrestricted forward movement of a head of the user, wherein the upper flange includes:
a first side segment opposing a second side segment, the first side segment and the second side segment configured to limit movement of the head in a sideways direction, and a rear segment configured to limit movement of the head in a rearward direction; and
at least one bumper affixed to the upper flange, wherein the at least one bumper is located on the upper flange and configured to exert a force on a back of the head or a side of the head during lateral flexion of the neck in a sideways direction or extension of the neck in a rearward direction to dampen movement of the head, wherein the at least one bumper includes a portion extended from a cavity of an upper surface of the upper flange.

16. An athletic collar comprising:
a lower flange configured to partially encircle a neck of a user, the lower flange including:
a back pad configured to contact an upper back region of the user,
a shoulder flap configured to provide a contact surface to be placed atop a shoulder of the user; and
an upper flange coupled to the lower flange and configured to encircle a portion of the neck and to allow unrestricted forward movement of a head of the user, wherein the upper flange includes:
a first side segment opposing a second side segment, wherein the first and second side segments are configured to gradually restrict movement of the head in a sideways direction to dampen movement of the head and to mitigate lateral hyperflexion of the neck; and
a rear segment configured to gradually restrict movement of the head to mitigate hyperextension of the neck; and
at least one bumper affixed to the upper flange, wherein the at least one bumper is located on the upper flange between an upper edge, a lower edge and a forward edge thereof, wherein the at least one bumper is configured to exert a force on a back of the head or a side of the head during lateral movement of the neck in a sideways direction or extension of the neck in a rearward direction to dampen movement of the head, wherein the at least one bumper is positioned on the upper flange and does not extend forward of the forward edge thereof.

17. The athletic collar of claim 16, wherein an upper edge of the upper flange is configured to be positioned to the side of the head of the user.

18. The athletic collar of claim 16, wherein an upper edge of the upper flange is configured to be positioned between a location to the side of an ear and a location to the side of a top of the neck of the user.

19. The collar of claim 16, wherein the upper flange is located to contact a lower region of the head, or to contact a helmet worn by the user, during lateral movement of the neck in a sideways direction or during extension of the neck in a rearward direction, but avoid contacting a bottom edge of the helmet to provide shock absorption without a fulcrum effect on the head.

20. The collar of claim 16, wherein the first side segment and the second side segment are positioned to provide clearance between the first and second side segments and the head, or a helmet worn by the user, and to limit sideways movement of the head, and the rear segment is positioned to provide clearance between the rear segment and the head or helmet and to limit rearward movement of the head.

* * * * *